United States Patent [19]

Prestrelski et al.

[11] Patent Number: 5,580,856
[45] Date of Patent: Dec. 3, 1996

[54] FORMULATION OF A RECONSTITUTED PROTEIN, AND METHOD AND KIT FOR THE PRODUCTION THEREOF

[76] Inventors: Steven J. Prestrelski, 1971 W. Middlefield Rd., Unit #5, Mountain View, Calif. 94043; Mei Z. Zhang, 444 Via Colinas, Thousand Oaks, Calif. 91362

[21] Appl. No.: 276,008

[22] Filed: Jul. 15, 1994

[51] Int. Cl.$^6$ .................. A61K 38/16; C07K 14/435; C07K 14/00; C07K 7/00
[52] U.S. Cl. .................. 514/21; 514/8; 514/12; 530/350; 530/351; 530/820; 530/827; 530/855; 530/324
[58] Field of Search ............... 530/350, 324, 530/820, 827, 855, 351; 514/8, 12, 21

[56] References Cited

U.S. PATENT DOCUMENTS

| | | | |
|---|---|---|---|
| 3,940,480 | 2/1976 | Suenaga et al. | 514/12 |
| 4,297,344 | 10/1981 | Schwinn et al. | 530/381 |
| 4,439,421 | 3/1984 | Hooper et al. | 424/177.1 |
| 4,478,829 | 10/1984 | Landaburu et al. | 514/21 |
| 4,717,717 | 1/1988 | Finkenaur | 514/21 |
| 4,891,319 | 1/1990 | Roser | 435/188 |
| 4,992,271 | 2/1991 | Fernandes et al. | 424/85.2 |
| 5,045,446 | 9/1991 | Goodrich, Jr. et al. | 435/2 |
| 5,078,997 | 1/1992 | Hora et al. | 424/85.2 |
| 5,093,117 | 3/1992 | Lawrence et al. | 424/1.49 |
| 5,183,746 | 2/1993 | Shaked et al. | 435/69.51 |
| 5,229,501 | 7/1993 | Keifer et al. | 530/399 |
| 5,242,772 | 9/1993 | Kato et al. | 430/49 |
| 5,310,727 | 5/1994 | Lattanzi et al. | 514/12 |
| 5,348,941 | 9/1994 | Middaugh et al. | 514/12 |
| 5,354,562 | 10/1994 | Platz et al. | 424/489 |

FOREIGN PATENT DOCUMENTS

WO93/00807 1/1993 WIPO.
WO93/12811 7/1993 WIPO.

OTHER PUBLICATIONS

Arakawa and Timasheff, *Archives of Biochemistry and Biophysics*, 224(1):169–177 (1983).
Arakawa and Timasheff, *Biochemistry*, 23:5912–5923 (1984).
Arakawa and Timasheff, *Methods in Enzymology*, 114:49–77 (1985).
Arakawa and Timasheff, *Biophysical Journal*, 47:411–414 (1985).
Busby et al., *The Journal of Biological Chemistry*, 256(23):12140–12147 (1981).
Carpenter et al., *Develop. Biol. Standard*, 74:225–239 (1991).
Carpenter et al., Keynote Address at 1994 ACS March Meeting in San Diego entitled "Infrared Spectroscopic Studies of Lyophilization–Induced Protein Aggregation".
Chang and Randall, *Cryobiology*, 29:632–656 (1992).
Charman et al., *Pharmaceutical Research*, 10(7):954–962 (1993).
Chen, *Drug Development and Industrial Pharmacy*, 18(11&12):1311–1354 (1992).
Cleland et al., *The Journal of Biological Chemistry and Molecular Biology, Inc.*, 267(19):13327–13334 (1992).
Franks, *Process Biochemistry*, 24:iii–vii (1989).
Franks, *Cryo–Letters*, 11:93–110 (1990).
Franks, *Bio/Technology*, 12:253–256 (1994).
Gombotz, *Pharmaceutical Research*, 11(5):624–632 (1994).

(List continued on next page.)

Primary Examiner—George C. Elliott
Assistant Examiner—Nancy J. Degen
Attorney, Agent, or Firm—Thomas D. Zindrick; Steven M. Odre

[57] ABSTRACT

Dried proteins are stabilized against loss of biological activity in formulations by adding an reconstitution stabilizer upon rehydration of the dried protein. A kit for producing and a formulation produced by dissolving the dried composition in a solvent containing the reconstitution stabilizer is also described.

25 Claims, 9 Drawing Sheets

OTHER PUBLICATIONS

Hora et al., *Pharmaceutical Research*, 9(1):33–36 (1992).
Itzutsu et al., *Pharmaceutical Research*, 10(8):1232–1237 (1993).
Manning et al., *Pharmaceutical Research*, 6(11):903–918 (1989).
Olson et al., *J. of Med. Chemistry*, 36(21):3039–3049 (1993).
Paborji et al., *Pharmaceutical Research*, 11(5):764–771 (1994).
Pearlman and Nguyen, In: D. Marshak and D. Lin (Eds.). Therapeutic Peptides and Proteins, Formuation, Delivery and Targeting, Cold Spring Harbour Laboratory, NY, pp. 23–30 (1989).
Pikal, *BioPharm*, Sep.:18–27 (1990).
Pikal, *BioPharm*, Oct.:26–30 (1990).
Prestrelski, *Biophysical Journal*, 65:661–671 (1993).
Santoro et al., *Biochemistry*, 31:5278–5283 (1992).
te Booy et al., *Pharmaceutical Research*, 9(1):109–114 (1992).
Townsend et al., *Pharmaceutical Research*, 7(10):1086–1091 (1990).
von Hippel and Wong, *The Journal of Biological Chemistry*, 240(10):3909–3923 (1965).
Yoshioka et al., *Pharmaceutical Research*, 10(10):1484–1487 (1993).

FORMULATION OF A RECONSTITUTED PROTEIN, AND METHOD AND KIT FOR THE PRODUCTION THEREOF

BACKGROUND OF THE INVENTION

Proteins are relatively unstable in the aqueous state and undergo chemical and physical degradation resulting in a loss of biological activity during processing and storage (Manning, et al. (1989), *Pharm. Res.*, 6:903–918). The process of drying (e.g., freeze-drying, spray drying and air drying) is often employed to stabilize proteins for long-term storage, particularly when the protein is relatively unstable in liquid formulations.

A lyophilization cycle is usually composed of three steps: freezing, primary drying and secondary drying (Williams and Polli (1984), *J. Parenteral Sci. Technol.* 38:48–59). In the freezing step, the protein solution is cooled until it is adequately frozen. Bulk water in the protein solution forms ice at this stage. This ice sublimes in the primary drying stage which is conducted by reducing chamber pressure below the vapor pressure of the ice using a vacuum. Finally, sorbed or bound water is removed at the secondary drying stage under reduced chamber pressure and elevated shelf temperature. The process produces a material known as a lyophilized cake. Thereafter the cake is reconstituted. The standard practice is to add back a volume of pure water (typically equivalent to the volume removed during lyophilization), although dilute solutions of antibacterial agents are sometimes used in production of pharmaceuticals for parenteral administration (Chen, *Drug Dev. Ind. Pharm.*, 18:1311–1354 (1992)).

Spray-drying is typically achieved by microdispersing a solution into a stream of hot gas. The solution is continously fed into the gas stream and microdispersion (atomization) is achieved through use of a pressurized air stream (Masters, in "Spray-Drying Handbook" (5th ed.) Longman Scientific and Technical, Essez, U.K., (1991), pp. 491–676). When applied to proteins, the temperature of the gas stream typically ranges from 80°–200° C. (Broadhead et al. (1992), *Drug Devel. Ind. Pharm.*, 18:1169–1206; and Mumenthaler et al. (1994), *Pharm. Res.*, 11:12–20).

Air-drying is typically performed by placing solutions at ambient temperature in a very low humidity environment. The solutions are continuously exposed to the low humidity air until they are sufficiently dry (Carpenter and Crowe (1988), *Cryobiology*, 25:459–470; and Roser (1991), *Biopharm*, 4:47–53).

Dried proteins are subject to conformational instability induced by the acute stresses encountered during drying. Protein stability during drying is a function of environmental factors which include temperature, humidity, pH, ionic strength, and solvent medium composition. Even when the protein survives drying without significant damage, damage may occur during storage of the dried product (Pikal, *BioPharm*, 27:26–30 (1990)). Damage to dried proteins is manifested after rehydration, for example, as a loss of protein solubility, aggregation, loss of activity in appropriate bioassays or in the case of enzymes, a loss of catalytic activity (Carpenter et al. (1991) *Develop. Biol. Standard.*, 74:225–239; WO 93/00807, to Carpenter; Broadhead et al. (1992), supra; Mumenthaler et al. (1994), supra; Carpenter and Crowe (1988), supra; and Roser (1991), supra).

Typical practices to improve protein stability are addressed by varying the formulation. For example, excipients are added to the protein solution or suspension prior to drying to improve the stability of the protein to the drying process, and to improve the storage stability of the dried product. (Carpenter et al. (1991), supra; and Pikal, (1990), supra). Commonly used excipients include sugars (e.g., sucrose, glucose, lactose, trehalose); amino acids (e.g., glycine, alanine, serine, proline, sodium glutamate, lysine, aminobutyric acid); proteins (e.g., human serum albumin, bovine serum albumin); glycerol; polyols (e.g., xylitol, mannitol, inositol, sorbitol); amines (e.g., betaine, sarcosine, trimethylamine N-oxide); salts (e.g., hydrogen chloride, phosphates, sodium acetate, magnesium sulfate, sodium chloride, ammonium sulfate and sodium sulfate); ethylene glycol; polyethylene glycol; 2-methyl-2,4-pentanediol and dimethylsulfoxide (Arakawa et al. (1990), *Cryobiology*, 27:401–415; Carpenter et al. (1991) supra; Pikal, (1990), supra; Broadhead et al. (1992), supra; Mumenthaler et al. (1994), supra; Carpenter and Crowe (1988), supra; and Roser (1991), supra).

While the use of additives has improved the stability of dried proteins, many proteins which are subject to drying and subsequent storage contain unacceptable or undesirable amounts of inactive, aggregated protein in the rehydrated formulation (Townsend and DeLuca (1983), *J. Pharm. Sci.*, 80:63–66; Hora et al. (1992), *Pharm. Res.*, 9:33–36; Yoshiaka et al. (1993), *Pharm. Res.*, 10:687–691; Izutsu et al. (1991), *Int. J. Pharm.*, 71:137–146; Liu et al. (1991), *Biotechnol. Bioeng.*, 37:177–184; Pikal et al. (1991), *Pharm. Res.*, 8:427–436; Townsend et al. (1990), *Pharm. Res.*, 7:1086–1090; Broadhead et al. (1992), supra; Mumenthaler et al. (1994), supra; Carpenter and Crowe (1988), supra; and Roser (1991), supra). This is particularly problematic when preparing pharmaceutical formulations, because aggregated proteins have been known to be immunogenic (Cleland et al. (1993), *Crit. Rev. Therapeutic Drug Carrier Systems*, 10:307–377; Robbins et al. (1987), *Diabetes*, 36:838–845; and Pinckard et al. (1967), *Clin. Exp. Immunol.*, 2:331–340).

Thus, there is a need to develop further means for increasing the amount of active protein from reconstituted formulations of dried proteins. It is to this and other objects that the present invention is directed.

SUMMARY OF THE INVENTION

The present invention encompasses a means for increasing the recovery of soluble protein, more specifically the native monomeric protein, or for decreasing the amount of aggregated protein upon reconstitution of a dried protein. In accordance with the present invention, there is provided: (1) a process for preparing a formulation, which comprises admixing a dried protein with an effective amount of at least one reconstitution stabilizer under conditions effective to reduce aggregation of the dried protein upon reconstitution; (2) a protein formulation prepared according to the above; (3) a kit for preparing protein formulation comprising a first container having a dried protein and a second container having a reconstitution stabilizer; and (4) a method comprising the step of administering into a patient an aqueous medicinal formulation as set forth above.

DETAILED DESCRIPTION OF THE INVENTION

Surprisingly, it has been discovered that a significant portion of the inactive proteins in formulations prepared from dried proteins can be the result of aggregation of otherwise undamaged protein upon reconstitution, i.e., during the rehydration step. Thus the present invention is directed to adding excipients which inhibit aggregation of otherwise undamaged protein which results from the rehydration of the dried protein. This method beneficially permits the use of reconstitution stabilizers which otherwise would not be suitable for drying because of deleterious effects upon the protein during prolonged storage or because of the instability of the excipient under drying conditions. Additionally, the rehydration of dried proteins may occur under conditions which aggregate the protein prior to dissolution of the excipients added prior to the drying step. The present method is directed to the addition of at least one dissolved reconstitution stabilizer to the dried protein prior to or upon rehydration, and thus prior to aggregation of the dried protein. As will be apparent, during the practice of the present invention one or more reconstitution stabilizers may be used.

The term "reconstitution stabilizer" means any excipient which is capable of preventing aggregation of a reconstituted protein in an aqueous medium. Excipients possessing the necessary characteristics for the present invention are well-known in the art and generally function by the mechanisms of charge replusion, steric hindrance, hydrophobic binding or specific high-affinity binding to the dried protein. Exemplary excipients include various osmolytes, various salts, water soluble synthetic and natural polymers, surfactants, sulfated polysaccharides, carrier proteins, buffers and the like (Manning et al. (1989), *Pharmaceutical Research*, 6:903–918; and Paborji, et al. (1994), *Pharmaceutical Research*, 11:764–771).

The osmolytes suitable for the present invention are those having the ability to increase the melting temperature of proteins. Exemplary osmolytes include amino acids, polyols (e.g., sorbitol, mannitol, xylitol and glycerol), sugars, sugar alcohols, sugar acids and the like. Exemplary osmolytes include, but are not limited to, amino acids (e.g., histidine, salts of histidine, glycine, salts of aspartic acid, salts of glutamic acid, salts of lysine, salts of arginine, serine, proline, alanine); polyhydric alcohols (e.g., sorbitol, inositol, mannitol, xylitol and glycerol); sugars (trehalose, lactose, sucrose, glucose, galactose, maltose, mannose and fructose) and methylamines (e.g., trimethylamine-N-oxide, N,N-dimethyl-glycine, aminobutyric acid, taurine, sarcosine, betaine or salts thereof). The concentration of the osmolyte in the rehydration formulation is preferably between about 0.01 weight percent to 10 weight percent and more preferably about 0.5 weight percent to 5 weight percent. Osmolytes are well known in the art and are manufactured by known methods (Santoro et al. (1992), *Biochemistry*, 31:5278–5283; Arakawa and Timasheff (1983), *Archives of Biochemistry and Biophysics*, 224:169–1771; Arakawa and Timasheff (1985), *Biophys. J. Biophysical Society*, 47:411–414).

The salts suitable for the present invention are those of the lyotropic series. Exemplary lyotropic salts include imidazole; tetraalkylammonium, alkaline metal, alkaline earth metal or ammonium salts of organic acids such as fumaric acid, succinic acid, oxalic acid, malic acid, citric acid, tartaric acid, and acetic acid (e.g., sodium fumarate, sodium succinate, sodium oxalate, sodium malate, sodium citrate, sodium tartarate or sodium acetate); or of mineral acids such as hydrochloric acid (e.g., sodium chloride); sulfuric acid (e.g., ammonium sulfate), phosphoric acid (e.g., sodium phosphate), and pyrophosphates (e.g., mono-sodium pyrophosphate, di-sodium di-hydrogenpyrophosphate and tetrasodium pyrophosphate). Additional salts also include ethylene-daimine tetraacetic acid (EDTA) or ethylene glycol-bis (β-aminoethyl ether) (EGTA). The concentration of the lyotropic salts in the rehydration formulation is preferably between about 1 mM to 1M, more preferably between about 10 mM to about 500 mM. Salts are well known in the art and are manufactured by known methods (Busby et al. (1981), *The Journal of Biological Chemistry*, 23:12140–12147; von Hippel and Wong (1965), *The Journal of Biological Chemistry*, 240:3909–3923; and Yoshioka, et al. (1993), *Pharmaceutical Research*, 10:1484–1487).

The water-soluble synthetic and natural polymers suitable for the present invention are those having molecular weights in the range of 100–150,000 and charged side groups at physiological pH or hydrophobic character. Exemplary water-soluble synthetic polymers include polyethylene glycol, polyvinyl pyrrolidone, polyvinyl pyrrdidae, poly(acrylic acid) and polyphosphates (e.g., including sodium tripolyphosphate and sodium polyphosphate). Exemplary natural polymers include homopolymeric and random copolymeric amino acids (e.g., salts of polylysine, salts of polyaspartic acid, salts of polyglutamic acid, salts of polyarginine, salts of polyhistidine, polyornithine and salts thereof). The concentration of the water-soluble synthetic polymers in the rehydration formulation is preferably between about 0.01 weight percent to 5 weight percent, more preferably about 0.1 weight percent to 2 weight percent. Water-soluble synthetic polymers are well known in the art and are manufactured by known methods (Gombotz, et al. (1994), *Pharmaceutical Research*, 11:624–632; Bell (1949), *Ind. Eng. Chem.*, 40:1464; Tsai et al. (1993), *Pharmaceutical Research*, 10:649–659); Cleland et al. (1992), *The Journal of Biological Chemistry*, 267:13327–13334; Alberty, et al. (1948), *J. Phys. & Colloid Chem.* 52:217; Crestfield. (1956), *Anal. Chem.*, 28:117; Rosemeyer and Shooter. (1958), *Biochem. J.*, 69:28; and Rosemeyer and Shooter., 5th Internat. Congr. Biochem., Moscow, Abstracts. 47 (1961)).

The surfactants suitable for the present invention are those which are non-denaturing and which typically enhance the solubility of proteins. Exemplary surfactants include polyethylene polypropylene glycol (e.g., pluronic), polyoxyethylene sorbitan mono-oleate (e.g., Tween-80), polyoxyethylene mono-laureate (e.g., Tween-20), hydroxypropyl β-cyclodextrin and N-octylglucoside. The concentration of the surfactants in the rehydration formulation is preferably between about 0.001 weight percent to 5 weight percent, more preferably about 0.01 weight percent to 1 weight percent. Surfactants are well known in the art and are manufactured by known methods (Cleland, et al. (1992), *The Journal of Biological Chemistry*, 267:13327–13334; and Charman, et al. (1993), *Pharmaceutical Research*, 10:954–961).

The sulfated oligo- and polysaccharides suitable for the present invention are those consisting of two or more saccharide units and containing one or more sulfation sites per saccharide unit. Exemplary sulfated polysaccharides include heparin, heparan sulfate, dextran sulfate, sucrose octasulfate, sulfated β-cyclodextrin, myo-inositol hexasulfate, polypentosan sulfate, fucoidan, chondroitin sulfate A, chondroitin sulfate B, chondroitin sulfate C and derivatives thereof. The concentration of the sulfated polysaccharides in the rehydration formulation is preferably between about 0.001 weight percent to 5 weight percent, more preferably between about 0.002 weight percent to 2.0 weight percent. Sulfated polysaccharides are well known in the art and are manufactured by known methods (Gospodarowicz, et al. (1986), *The Journal of Cellular Physiology*, 128:475–484; Volkin et al. (1993), *Arch-Biophys. Biochem.*, 300:30–41).

The carrier proteins suitable for the present invention are those water soluble proteins which are biologically inert with respect to the dried protein and which generally have a molecular weight greater than 5000. Exemplary carrier proteins include phosvitin and serum albumin. The concentration of the carrier proteins is between about 0.05 weight percent to 0.5 weight percent, more preferably about 0.02 weight percent to 0.1 weight percent. Proteins are well known in the art and are manufactured by known methods (Taborsky (1974), *Advanced Protein Chemistry*, 28:50–78).

The buffers suitable for the present invention are those having pH buffering capacity in the range of from about pH 1 to pH 13 and are compatible with the dried protein. Exemplary buffers include phosphoric acid buffers, citric acid buffers, Good's buffers (e.g., morpholinoethane sulfonic acid (MES) and homopipes) and the like. The concentration of the buffer in the rehydration formulation is preferably between about 1 mM to 1M, more preferably about 10 mM to 200 mM. Buffers are well known in the art and are manufactured by known methods (Good et al. (1966), *Biochemistry*, 5:467; and Donald et al., 1990 CALBIOCHEM catalog, pages 3–24, CALBIOCHEM Corporation, La Jolla, Calif. 92037).

A further embodiment of the present invention involves the pre-dried formulation containing minor amounts of additives, such as substances that maintain physiological or otherwise optimal pH, isotonicity and stability. Such materials include pH buffers, preservatives, tonicity adjusting agents, anti-oxidants, other polymers (e.g., viscosity adjusting agents or extenders) and excipients to stabilize the labile protein against the stresses of drying and storage of the dried product. Specific illustrative examples of such additives include phosphate, citrate, or borate buffers; thimerosal; sorbic acid; methyl or propyl paraben, and chlorobutanol preservatives; sodium chloride: polyvinyl alcohol, polyvinyl pyrrolidone; mannitol, dextrose, dextran, lactose, sucrose, ethylene diamine tetra-acetic acid, and the like. Suitable formulations, known in the art, (*Remington's Pharmaceutical Sciences* (latest edition), Mack Publishing Company, Easton, Pa.; Arakawa et al. (1990), supra; Carpenter et al. (1991), supra; and Pikal (1990), supra).

The present invention may suitably be applied to any protein subjected to freeze-drying or other forms of drying such as spray-drying and air drying. Exemplary proteins for use in the present invention include, but are not limited to, growth factors, hormones, enzymes, clotting factors, structural proteins, complement factors, antibodies and antigens; pesticides (e.g., herbicides and fungicides) and bacterial toxins. Specifically, such proteins include Erythropoietin; Granulocyte Colony Stimulating Factor; Granulocyte Macrophage Colony Stimulating Factor; Epidermal Growth Factor; Acidic Fibroblast Growth Factor; Basic Fibroblast Growth Factor; Keratinocyte Growth Factor; Interferon-alpha; Interferon-gamma; Interleukins (IL alpha, IL-1 beta, IL-2, IL-3, IL-4, IL-6, IL-7, IL-8, IL-9, IL-10, IL-11); Factor VIII; Antithrombin III; Insulin; Tumor Necrosis Factor-alpha; Tumor Necrosis Factor-beta; Transforming Growth Factor-beta; Tissue Plasminogen Activator; Platelet-derived Growth Factor; Urokinase; Streptokinase; Peroxidase; RNA Polymerase; T7 DNA Polymerase; Taq DNA polymerase; Fibrinogen; Thrombin; Alcohol dehydrogenase; Alkaline phosphatase; Arginase; Ascorbate oxidase; Cholesterol esterase; Cholinesterase; Collagenase; DNase I; DNase II; Enterokinase; Glucose-6-phosphate dehydrogenase; Glucose oxidase; Glucose Isomerase; Glutamate dehydrogenase; Glyceraldehyde-3-phosphate dehydrogenase; Hexokinase; Lactate Dehydrogenase; Malate dehydrogenase; PEP carboxylase; RNase A; Soybean trypsin inhibitor; Urease; Xanthine oxidase; Superoxide dismutase; Fibronectin;

Restriction Endonucleases; Reverse transcriptase; M-MuLV; Monoclonal Antibodies; OKT3; HA-1A; BMA 031; CAMPATH-1; anti-TAC; Thrombopoietin; subtilisins; *Bacillus thuringiensis* crystal protein and the like.

As should be apparent, the efficacy of an individual reconstitution stabilizer is protein dependent, but the selection and optimization of appropriate reconstitution stabilizers (as well as excipients in the pre-drying formulation) for a particular protein will be within the skill of ordinary artisans and obtainable with only routine experimentation. Thus, strategy must take into consideration that certain excipients (alone or in combination) may be incompatible with certain proteins (Townsend and DeLuca (1990), *Pharmaceutical Research*, 7:1086–1097; Izutsu, et al. (1993), *Pharmaceutical Research*, 10:1232–1237; te Booy, et al. (1992), *Pharmaceutical Research*, 9:109–114). Thus excipients in the pre-drying formulation, the reconstitution formulation, or both should be selected to be compatible with the dried protein.

The dried protein and an effective amount of the reconstitution stabilizer are admixed under conditions effective to reduce aggregation of the dried protein upon reconstitution with the reconstitution medium (e.g., a solvent and optionally other components such as antibacterials). The reconstitution stabilizer may be admixed with the dried protein at a suitable time before, during or after reconstitution; preferably the reconstitution stabilizer will be pre-dissolved in the reconstitution medium. The dried protein is reconstituted at a temperature which is above the freezing point of the reconstitution medium, but which will not degrade the protein and which will not be deleterious to the reconstitution stabilizer; preferably the temperature will be between about 2° C. to 50° C. The time taken to mix the reconstitution stabilizer and the dried protein should be for a sufficient period to prepare a suitable admixture; preferably mixing will be for between about 1 to 30 minutes. Generally, the reconstituted formulation, particularly when it is a medical formulation, is used soon after reconstitution.

In another embodiment, the present invention is directed to a kit for preparing an aqueous protein formulation, which kit contains both a first container containing a dried protein and a second container containing an aqueous formulation comprising a reconstitution stabilizer. As for the concentration of the protein in the solution, the solution volume which is charged into each container, and the capacity of the containers (interrelated parameters which can be suitably modified, depending upon the desired concentration of active principle in the end dosage unit), these may vary within wide ranges.

In yet another embodiment, the present invention is directed to single dose administration unit of a medicinal formulation, which can be safely administered parenterally or orally to treat a disease in a warm-blooded animal (such as a human). Such medicinal formulation may be in the form of a lyophilized or otherwise dehydrated therapeutic or diagnostic which can be reconstituted by the addition of a physiologically acceptable solvent. The solvent may be any media such as sterile water, physiological saline solution, glucose solution or other aqueous solvents (e.g., alcohols such as ethyl, n-propyl or isopropyl, butyl alcohol or mixtures thereof) which is capable of dissolving the dried composition, which is compatible with the selected administration route and which does not negatively interfere with the active principle and the reconstitution stabilizers employed. In a specific embodiment, the present invention is directed to a kit for producing the single-dose administration unit, The concentration of protein in the pharmaceutical single-dose administration unit (bearing in mind that a suitable vial capacity, according to conventional pharmaceutical practice, is generally comprised between 1 and 5 ml and preferably between 1 and 2.5 ml.) is generally within the range of from about 0.05 to about 20,000 micrograms per milliliter (μg/ml) of aqueous formulation (that is, the formulation that has been reconstituted after dehydration).

The following examples illustrate various features of the present invention.

EXAMPLES

*E. coli* derived recombinant hKGF (rhKGF) was used in the following examples. Recombinant human KGF (rhKGF) has been cloned and expressed in *E. coli* and contains 163 amino acid residues.

Human interleukin-2 analog (IL 2-Ala125) used in this study was produced recombinantly (Arakawa, et al.(1986), *Biochemistry*, 25:8274–8277). The protein was purified by a series of standard chromatography procedures, oxidized to form an intramolecular disulfide bond, and stored in 10 mM sodium acetate buffer (pH 4.0) containing 5% glucose. The final product displayed a high purity (>95%) by SDS-PAGE under reducing and non reducing conditions.

Ribonuclease A (Type X-A, from bovine pancreas, R-5250) was purchased from Sigma Chemical Co. (St. Louis, Mo.) and ribonuclei acid (yeast) was from Boehringer Mannheim (Indianapolis, Ind.).

All chemicals used were either analytical grade or USP grade. Sulfated β-cyclodextrin was purchased from American Maize Products Company (Hammond, Ind.). Sodium polyphosphates and disodium dihydrogen pyrophosphate were purchased from Aldrich Chemical Company, Inc. (Milwaukee, Wis.). Tween-20 was purchased from Bio-Rad Laboratories (Richmond, Calif.). All other sulfated polysaccharides, amino acids, salts, and surfactants as well as the disodium salt of ethylenediamine tetraacetic acid (EDTA) were purchased from Sigma Chemical Co. (St. Louis, Mo.). All references in the text to solute concentration are on a weight-to-volume (w/v) percentage basis unless specifically stated otherwise.

Sample Preparation, Filling and Freeze-Drying:

Recombinant keratinocyte growth factor at a concentration of 3–4 mg/ml in phosphate-buffered saline (PBS) was dialyzed against 10 mM potassium phosphate buffer, pH 7.5, in Spectra/Por 7 cellulose dialysis tubing (Spectrum Medical Industries, Inc., Los Angeles, Calif. 90060) at 4° C. Interleukin-2 (Ala 125) at a concentration of 8 mg/ml in 20 mM citrate buffer, pH 4.0 was dialyzed against 10 mM MES, pH 4.0 over night at 4° C. IL-2 solutions with pHs other than 4.0 were prepared by a sufficient number of buffer changes at desired pHs several hours before lyophilization. RNase A at a concentration of 3–4 mg/ml in 200 mM sodium phosphate buffer, pH 6.5, was dialyzed against 200 mM sodium phosphate buffer, pH 10.0, at 4° C.

Figure 5A:
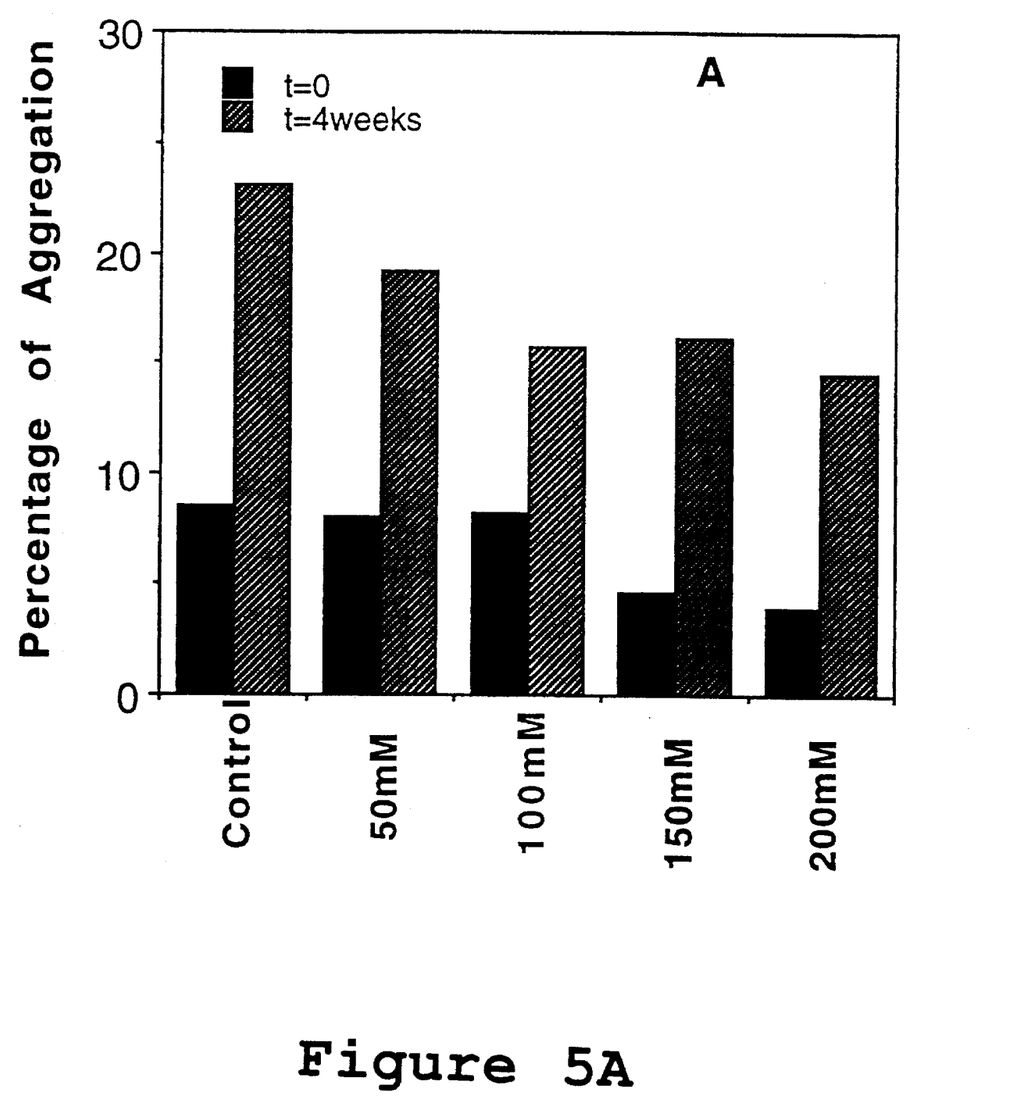
FIGS. 5A, 5B and 5C show the effects of salt concentration on KGF aggregation stored at 45° C. and reconstituted with: (5A) NaCl, (5B) $NH_4SO_4$ or (5C) Na citrate solutions, respectively. Lyophilized KGF samples in FIGS. 5A and 5B contain 4.5% mannitol, 0.5% sucrose in 10 mM potassium phosphate buffer, pH 7.0 and were reconstituted with 1 mL reconstitution medium. Lyophilized KGF samples in FIG. 5C contain 10 mM potassium phosphate buffer, pH 7.0. Each reconstituted sample was centrifuged (14000 g, 20 minutes at 4° C.) and the absorbance of the supernatant of the sample was obtained.
Figure 5B:
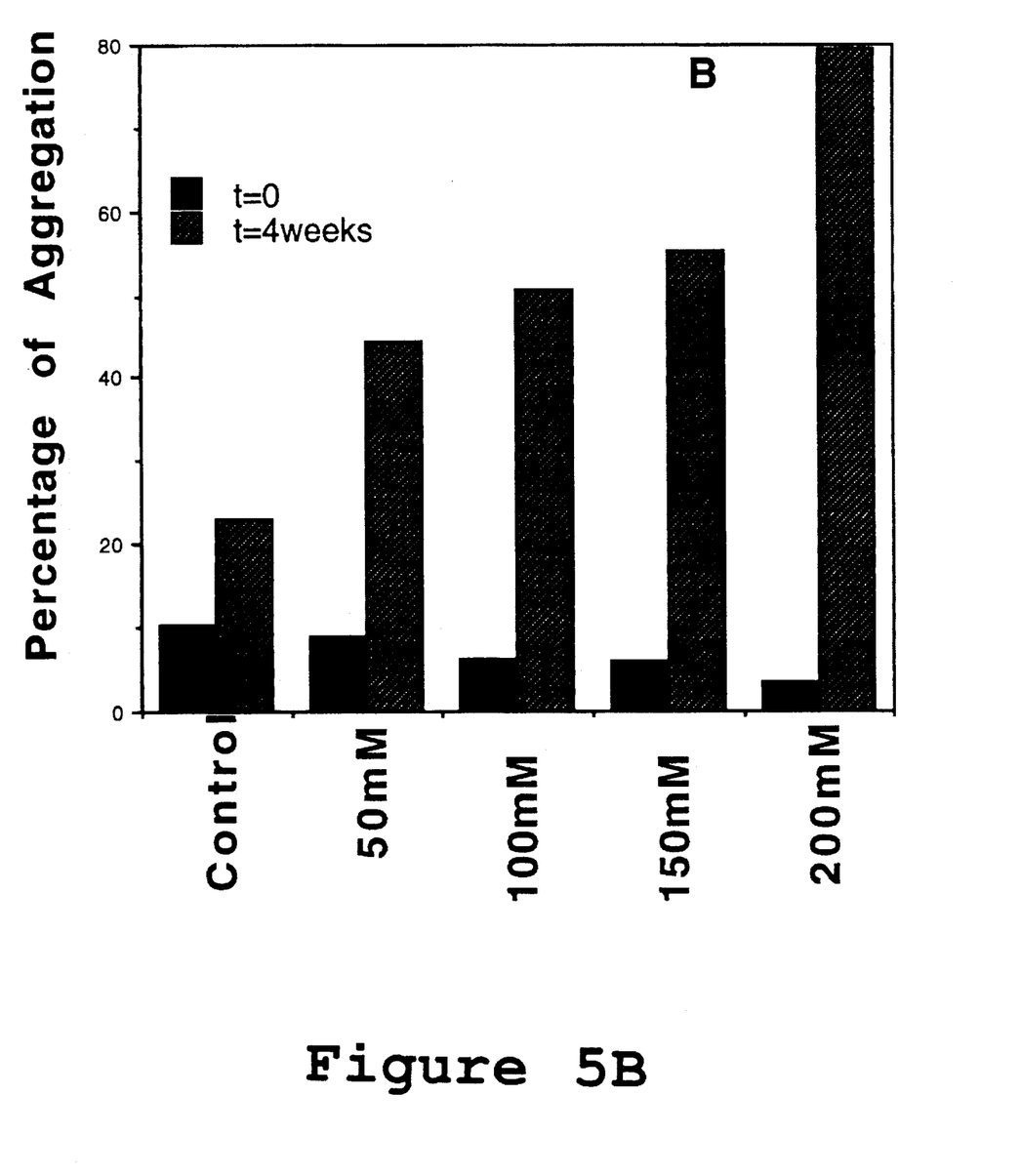

Protein concentration was determined spectrophotometrically using an extinction coefficient (ε=1.03, rhKGF; ε=0.88, IL-2; ε=0.67, RNase) at 280 nm. Sufficient buffer was added to the stock solution to adjust the protein concentration (0.5 mg/ml, rhKGF; 0.8 mg/ml, IL-2; 1.5 mg/ml, RNase A) in the desired pH buffers.

rhKGF samples in FIGS. 5A and 5B were lyophilized from a buffer containing 4.5% mannitol, 0.5% sucrose. All lyophilized IL-2 samples in Table III contained 5% mannitol.

The solutions were filtered through a 0.22 μm-pore size filter (Millex GV filter, Millipore Corp., Bedford, Mass.) and filled in 1 ml aliquots into sterile, 3 ml glass vials (Baxter Diagnostics, Inc., Scientific Products Division, McGaw, Ill. 60085-6787). Butyl rubber freeze-dry stoppers (1-mm diameter, West Co., Phoenixville, Pa.) were inserted halfway into the vials and the vials were transferred to the freeze-dryer shelves (FTS Systems, Stoneridge, N.Y.), which had been pre-cooled to −50° C. The temperature of the samples was then maintained at −50° C. for two hours. Primary drying was carried out at a vacuum of less than 100 mTorr, a condenser temperature of less than −60° C., and a shelf temperature of −45° C. for 12 hours followed by a shelf temperature of −10° C. for 10 hours. Secondary drying was at +20° C. for 10 hours. At the end of the freeze-drying cycle, all the vials were sealed with stoppers in the chamber under vacuum. Aluminum overseals were crimped into place prior to storage. The freeze-dried samples were stored at 45° C., and removed at appropriate intervals for various analytical measurements, described below.

Aggregation measurements:

The amount of soluble protein was monitored by absorbance at 280 nm using a Beckman DU 650 UV-visible spectrophotometer corrected for light scattering (Beckman Instruments, Fullerton, Calif.). Each lyophilized sample was reconstituted in 1 mL of water or additive solutions, followed by centrifugation (14000 g, 20 minutes at 4° C.). The absorbance of the supernatant of the sample was obtained. The degree of aggregation (expressed as percent of aggregate) was calculated by comparing the absorbance of the supernatant to the absorbance of the pre-lyophilized sample. The "stabilization ratio" was defined here as the amount of soluble protein recovered when the lyophilized protein was reconstituted with an additive solution normalized to protein recovered when reconstituted in water alone. Thus, a value of 1.0 indicates that the additive has no effect on aggregation. Values greater than 1.0 indicates enhanced stabilization, while values less than 1.0 indicates destabilization.

Analysis of Soluble Protein:

HP-SEC of protein was carried out at 25° C. on a Pharmacia Superdex 75 column (10×30 cm I.D., Pharmacia Biotech, Inc., Alameda, Calif.). The quantitation of KGF monomeric peak was accomplished using Hewlett-Packard 1090 series II with a diode array detector and HP 1047A refractive index detector. PBS buffer plus 1M NaCl, pH 7.0 (isocratic conditions) was used as the mobile phase at a flow rate of 0.5 mL/min. This high salt elution buffer was required to dissociate additives (e.g., heparin), which potentially bind to the proteins, and to reduce non-specific interaction of the proteins with the column matrix. Elution of protein was followed by absorbance at 280 nm and by refractive index change. The sample proteins (100 μL) were injected onto the system by auto-injection.

The molecular weight of the eluted peaks from HP-SEC was determined by using an on-line light scattering/chromatography system. The eluent was monitored by three detectors in series: a Knauer A293 absorbance monitor at 280 (Knauer Wissenschaftl Geratebau Dr. Ing. H. Knauer GmbH, Berlin, Germany), a Wyatt mini-Dawn laser light scattering detector (Wyatt Tedchnology Corporation, Santa Barabara, Calif.) and a refractive index detector operating at 650 nm (Polymer Laboratories PL-RI, Amherst, Mass.). The molecular weight of the elution peak was calculated from the ratio of the light scattering to refractive index signals (Tagaki (1990), *J. Chromatogr.*, 506:409–416). Ribonuclease, ovalbumin, and bovine serum albumin (monomer) were used to determine instrument constants.

Enzymatic Activity Measurements:

An enzymatic activity assay was performed to test the effect of the additives on the Ribonuclease A biological activity. The activity of reconstituted RNase A was determined at 30° C. using the substrate nucleic acid as described by Kunitz (Kunitz (1946), *J. Biol. Chem.*, 164:563–568). The remaining relative activities were expressed as percentages of the pre-lyophilized aqueous sample.

EXAMPLE 1

Effect of Reconstitution Stabilizers on KGF Aggregation

Lyophilized rhKGF was exposed to accelerated storage conditions (high temperatures and long periods of incubation) and the loss of soluble protein after reconstitution in the presence or absence of the additives was determined.

A. Sulfated Polysaccharides

Figure 1:
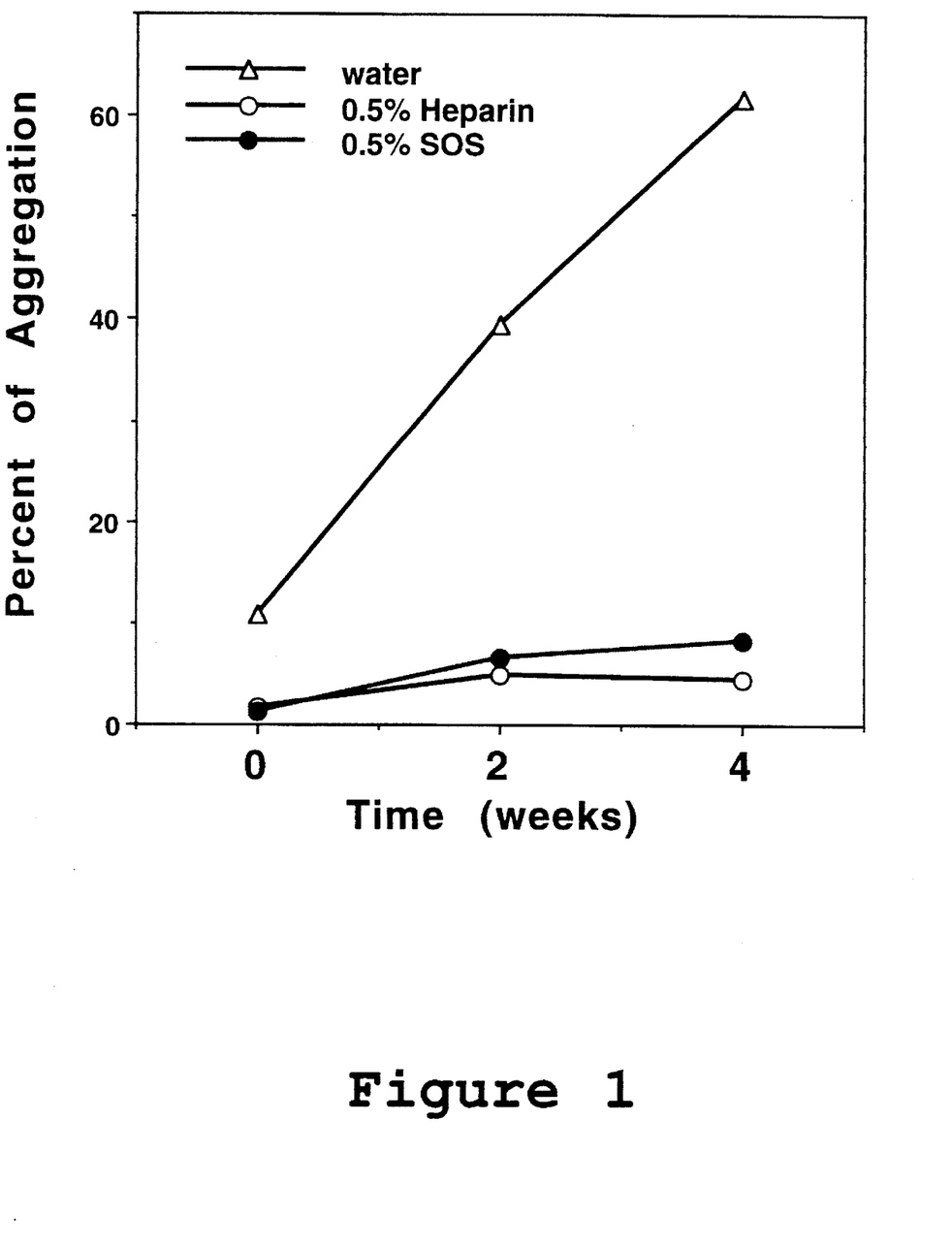
FIG. 1 shows the amount of aggregation for lyophilized KGF before or after storage at 45° C. upon reconstitution with 1 mL water, or 0.05% heparin (16K), or 0.05% sucrose octalsulfate (SOS) solution. KGF samples at 0.5 mg/mL were lyophilized from 10 mM potassium phosphate buffer, pH 7.5. Each reconstituted sample was centrifuged (14000 g, 20 minutes at 4° C.) and the absorbance of the supernatant of the sample was obtained. The degree of aggregation (expressed as percent of aggregate) was calculated by comparing the absorbance of the supernatant to the absorbance of the pre-lyophilized sample.
Figure 2:
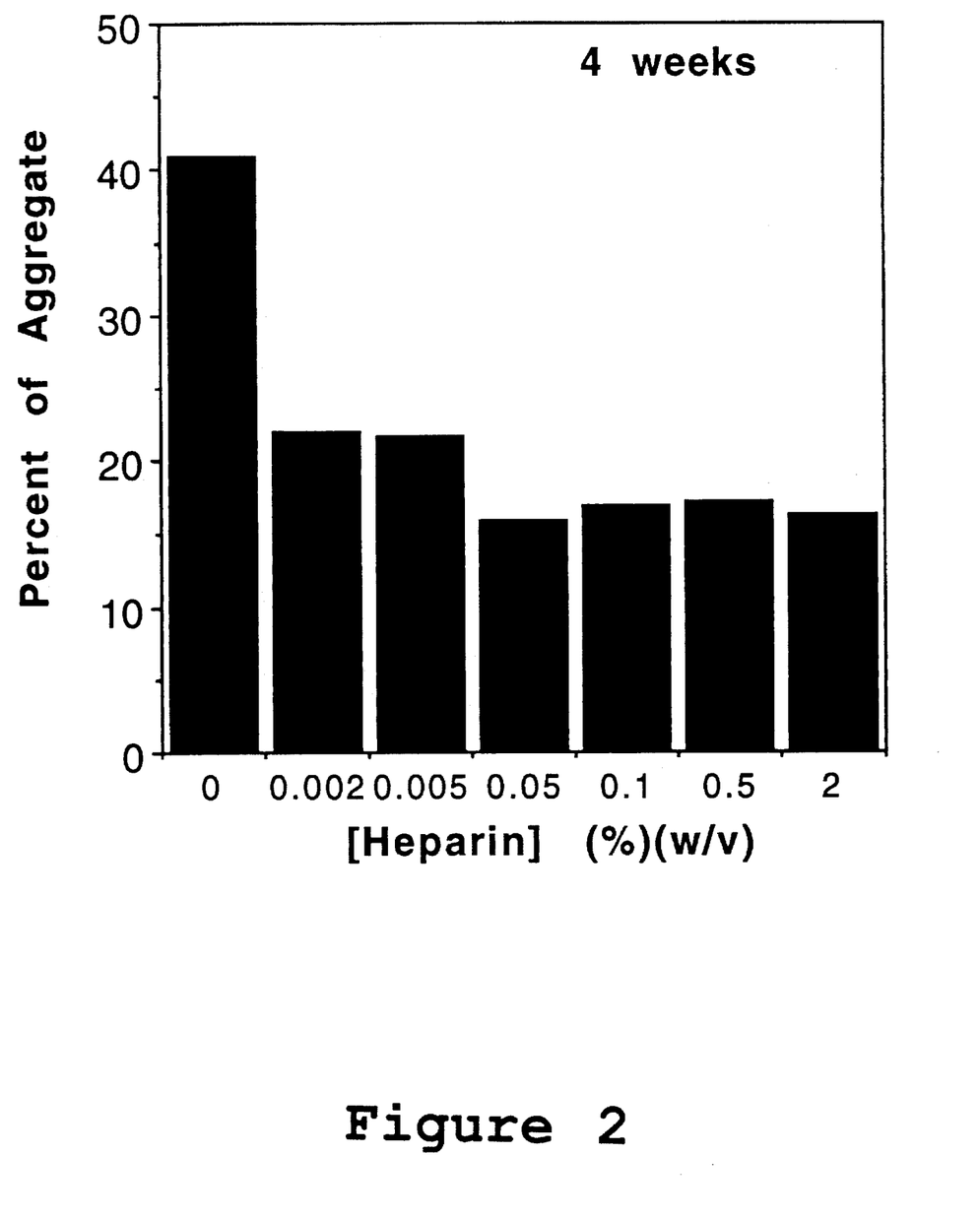
FIG. 2 shows the effects of 16K heparin concentration on KGF aggregation after 4 weeks storage at 45° C. and reconstitution with 1 mL heparin solution. Lyophilized KGF samples at 0.5 mg/mL contain 10 mM potassium phosphate buffer, pH 7.0. Each reconstituted sample was centrifuged (14000 g, 20 minutes at 4° C.) and the absorbance of the supernatant of the sample was obtained.

FIG. 1 shows that the extent of aggregation increased with increased storage time when the lyophilized rKGF was reconstituted with pure water. However, when the lyophilized KGF was rehydrated with water containing either heparin or sucrose octasulfate (SOS), aggregation was only 10 to 15% of that rehydrated with water. The effect of heparin concentration on the extent of aggregation upon reconstitution is shown in FIG. 2. Heparin at a concentration as low as 0.002% was sufficient to reduce aggregation. Further reduction in aggregation was observed with increasing heparin concentrations up to 0.05%. Above 0.05%, no additional reduction of aggregate was observed. This suggests that the remaining insoluble protein has been irreversibly altered.

B. Sulfated Polysaccharides and Water Soluble Polymers

Figure 3:
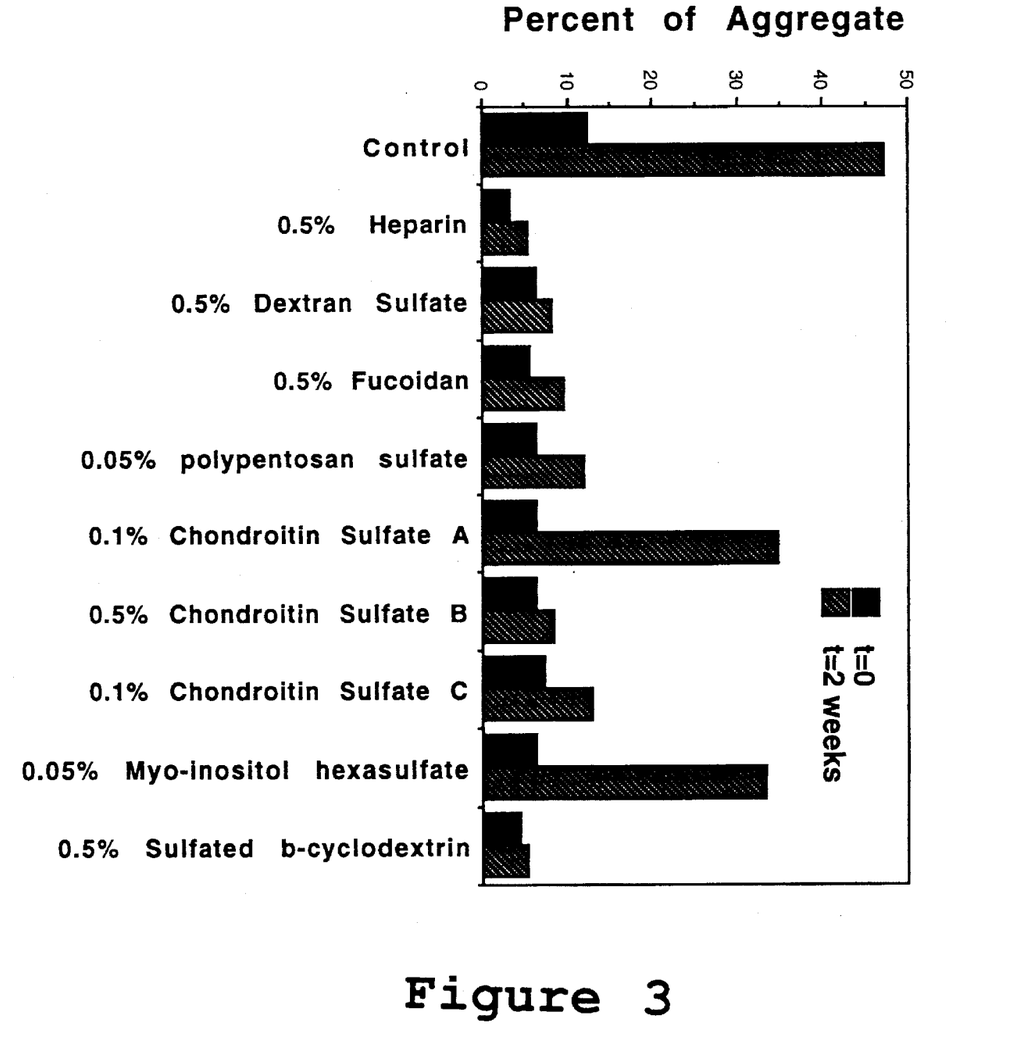
FIG. 3 shows the amount of aggregation for lyophilized KGF stored at 45° C. for two weeks upon reconstitution with 1 mL solution containing the sulfated polysaccharides. Lyophilized KGF samples contain 5% mannitol in 10 mM potassium phosphate buffer, pH 7.0. Each reconstituted sample was centrifuged (14000 g, 20 minutes at 4° C.) and the absorbance of the supernatant of the sample was obtained.

A variety of heparin-like sulfated polysaccharides, small sulfated compounds and other highly charged compounds (e.g., phosphorylated molecules) were added to a reconstitution medium and screened for their effects on the extent of aggregation upon reconstitution. A summary of these reconstitution experiments in terms of the extent of aggregation is illustrated in FIG. 3 (heparin-like sulfated polysaccharides, small sulfated compounds) and in FIG. 4 (phosphorylated molecules). In each case the reconstitution stabilizers decrease the extent of aggregation.

C. Osmolytes, Water Soluble Polymers, Surfactants and Lyotropic Salts

Table I shows the extent of aggregation upon reconstitution with a variety of osmolytes, water soluble polymers, surfactants and lyotropic salts known to stabilize proteins nonspecifically during freeze-drying and/or subsequent storage.

TABLE I

Amount of soluble KGF after two weeks at 45° C. storage and reconstitution.

| Reconstitution Medium | Stability Ratio |
| --- | --- |
| Control | 1.0 |
| Osmolytes | |
| 10 mM Histidine | 1.18 |
| 60 mM Histidine | 1.06 |
| 66 mM Glycine | 1.08 |
| 660 mM Glycine | 1.52 |
| 3 mM sodium aspartate | 1.36 |

TABLE I-continued

Amount of soluble KGF after two weeks at 45° C. storage and reconstitution.

| Reconstitution Medium | Stability Ratio |
|---|---|
| 15 mM sodium aspartate | 1.74 |
| 30 mm sodium glutamate | 1.17 |
| 27 mM lysine hydrochloride | 1.11 |
| Water-Soluble Polymers | |
| 0.5% Poly-L-glutamic | 1.30 |
| 0.5% Poly-L-lysine | 1.11 |
| 0.1% Poly (acrylic acid) | 1.13 |
| 0.05% Poly (lys, ala) | 1.04 |
| 0.5% PEG 300 | 1.17 |
| 2.0% PEG 300 | 1.19 |
| Surfactants | |
| 0.05% Pluronic | 1.03 |
| 0.5% Tween-20 | 1.42 |
| 0.05% N-Octylglucoside | 1.09 |
| 1.0% Hydroxypropyl β-cyclodextrin | 1.25 |
| Lyotropic Salts | |
| 10 mM Imidazole (HCl) | 1.23 |
| 50 mM Imidazole (HCl) | 1.50 |
| 0.05% EDTA | 1.20 |

As seen in Table I, samples containing the various reconstitution stabilizers show less loss of soluble rhKGF, as indicated by stabilization ratios greater than 1.0.

D. Lyotropic Salts

Figure 5C:
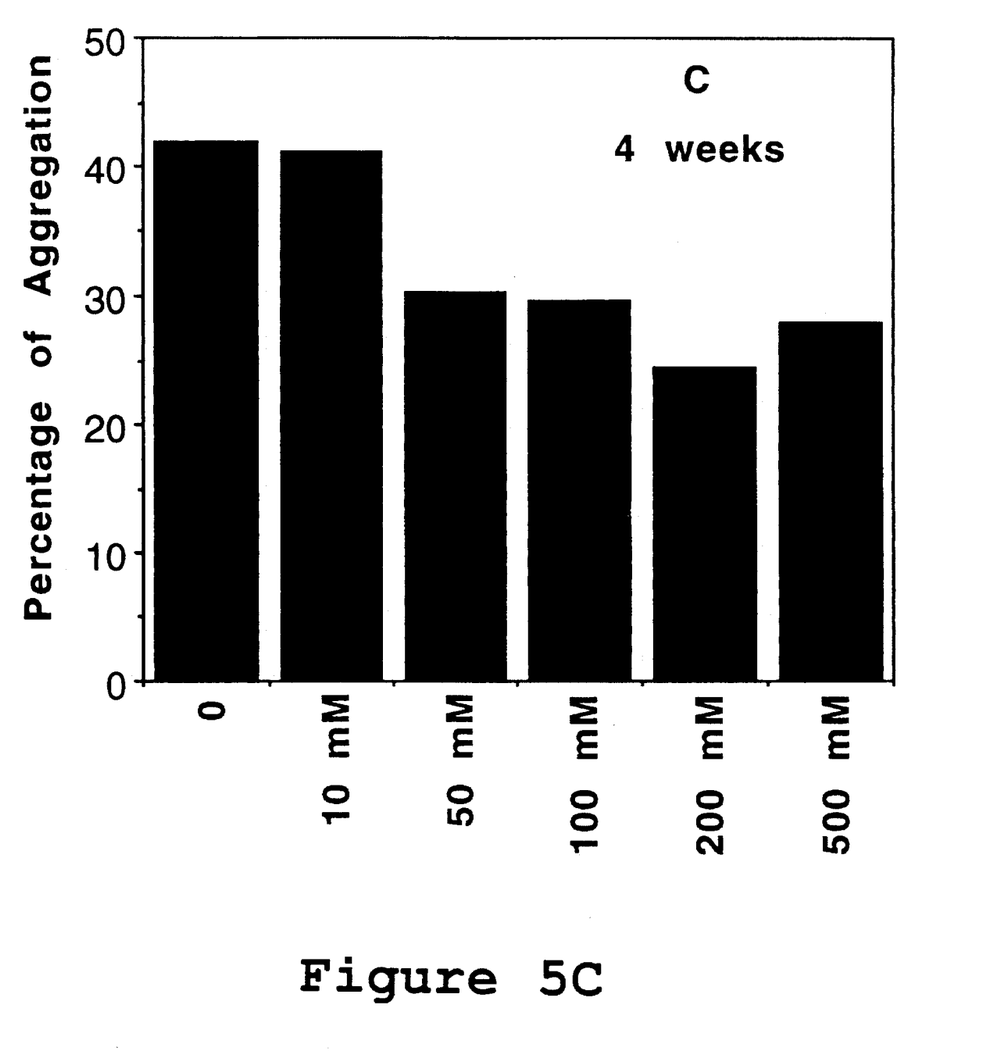

FIGS. 5A, B and C show the degree of rhKGF aggregation when rehydrated in the presence of various amounts of sodium chloride (NaCl), ammonium sulfate (($NH_4$)$SO_4$) and sodium citrate, respectively, versus control (water alone). Measurements were taken immediately after lyophilization or after fourteen days of storage at 45° C. Table I shows that other salts such as imidazole at moderate concentration (50 mM) were effective in reducing aggregation accompanying reconstitution.

E. Soluble Protein Analysis

The amount of soluble protein may be enhanced by various additives. However, proteins can assume different conformations or oligomeric states, all of which might be soluble. In order to examine the entity of the soluble protein, HP-SEC, a protein conformation and size sensitive technique, was carried out. The results are summarized in Table II.

Figure 6:
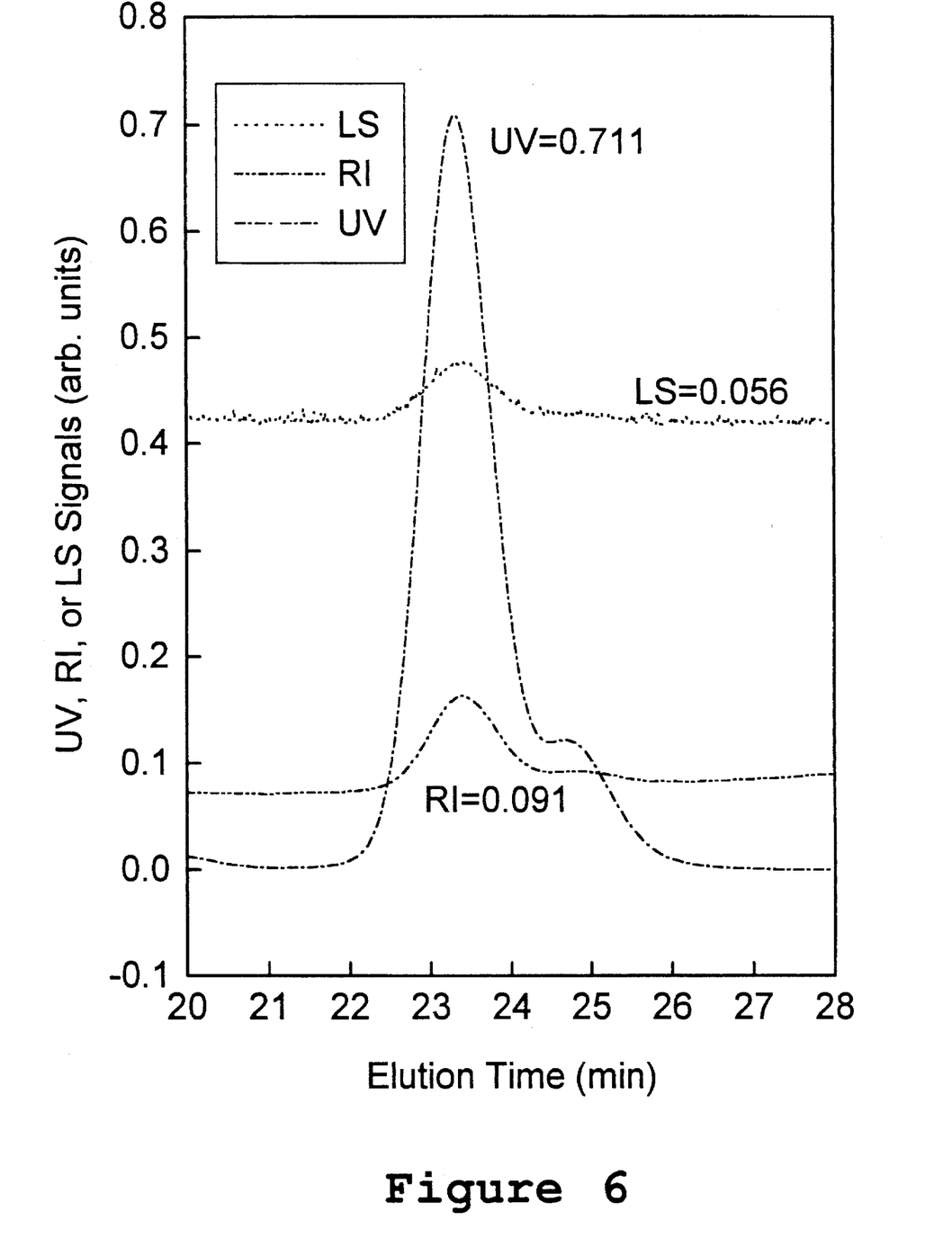
FIG. 6 shows the effects of pH on aggregation of a lyophilized IL-2 formulation stored at 45° C. for three weeks upon reconstitution with 1 mL buffers. The lyophilization formulation contained IL-2 and 5% mannitol in 10 mM potassium phosphate buffer, pH 7.0. Each reconstituted sample was centrifuged (14000 g, 20 minutes at 4° C.) and the absorbance of the supernatant of the sample was obtained.
Figure 7:
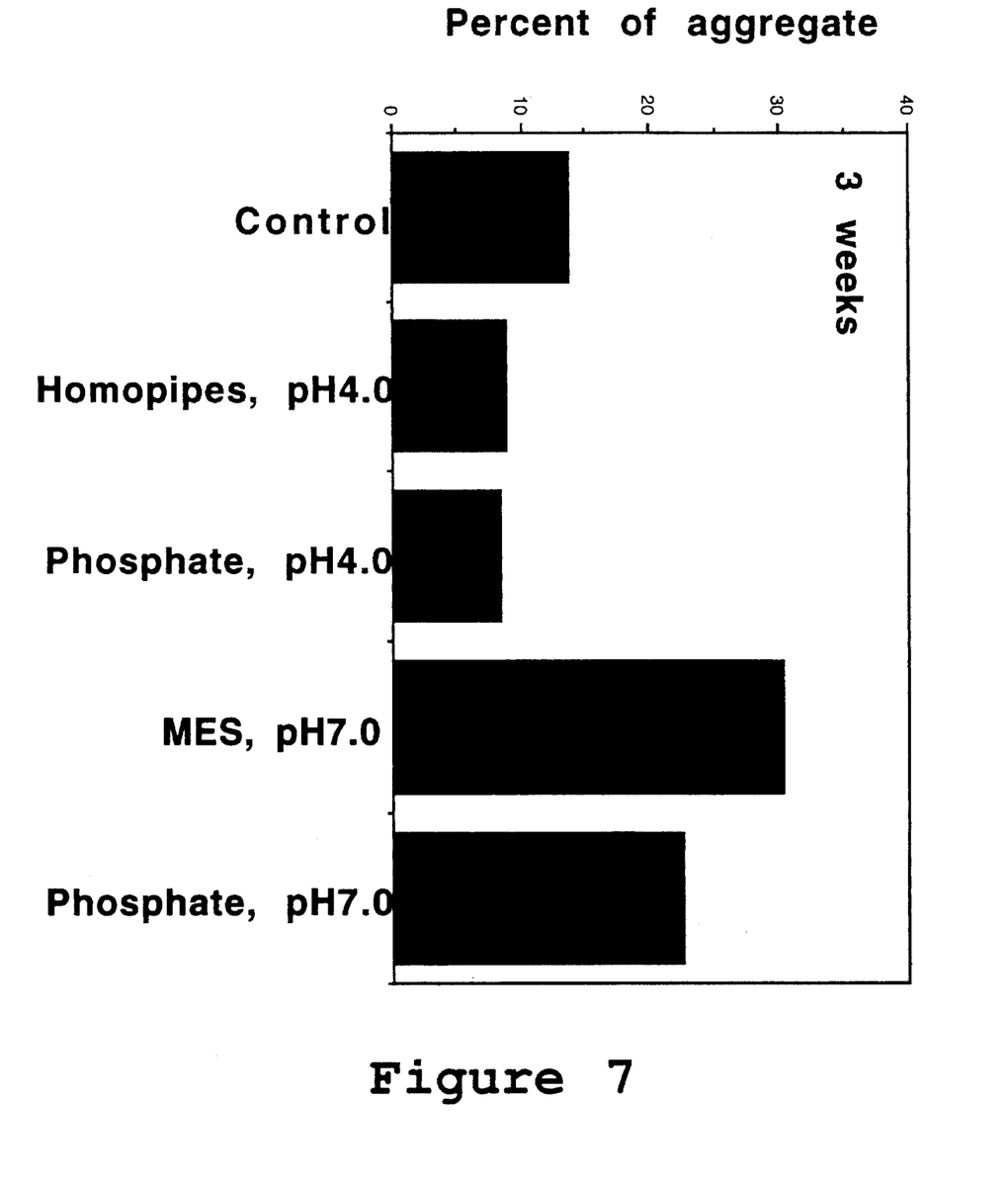
FIG. 7 shows a typical high-performance-size exclusion chromatography (HP-SEC) chromatogram of the reconstituted KGF sample with light-scattering, refractive index, and absorbance detection. The lyophilized KGF samples at 0.5 mg/mL contained 10 mM potassium phosphate buffer, pH 7.0.

The molecular weight of the peak was determined by light scattering technique and was calculated to be 18.5 k, corresponding to the monomeric form of KGF (FIG. 6).

TABLE II

HP-SEC peak area of soluble KGF after 45° C. storage and reconstitution sample.

| | 2 Weeks | | 4 Weeks | |
|---|---|---|---|---|
| | Peak Area | Soluble Protein | Peak Area | Soluble Protein (mg/mL) |
| Control | 2771 | 0.48 | 2528 | 0.44 |
| Heparin | 3200 | 0.56 | 2960 | 0.52 |
| Sulfated β-cyclodextrin | 2959 | 0.51 | 2678 | 0.47 |
| Sodium polyphosphate | 3245 | 0.56 | 2953 | 0.51 |

The reconstituted KGF samples eluted at the elution position of the aqueous, native KGF sample (23 minutes), suggesting that the reconstituted protein eluting in this peak has the characteristic of the native KGF. The amount of native protein calculated from the peak area, relative to the peak area of known protein concentration, decreased for the sample reconstituted with water, while the samples reconsitituted with water containing the indicated additives showed increased recovery of the native protein. In fact, in each sample the amount of protein calculated is in agreement with the amount of soluble protein, indicating that the protein remaining in the supernatant is the native, monomeric protein.

EXAMPLE 2

Effect of Reconstitution Stabilizers on IL-2 Aggregation

Lyophilized IL-2 (Ala 125) was exposed to accelerated storage conditions (high temperature and long period of incubation) and the loss of soluble protein after reconstitution in the presence or absence of the additives was determined. This protein is relatively hydrophobic, and as such, aggregation occurs upon lyophilization and storage at neutral pH (Hora, *Develop. Biol. Standard.*, 74:295–306 (1991)).

A. Sulfated polysaccharides, Osmolytes, Water Soluble Polymers, Surfactants and Proteins A variety of compounds were tested for their capacity to reduce IL-2 aggregation upon reconstitution. The results are summarized in Table III.

TABLE III

Amount of soluble IL-2 after two weeks of storage at 45° C. upon reconstitution.

| Reconstitution medium | Stability ratio |
|---|---|
| Control | 1.00 |
| Sulfated polysaccharides | |
| 0.5% Heparin | 2.80 |
| 0.5% Heparin + 0.05% EDTA | 3.41 |
| 0.5% Dextran Sulfate | 2.91 |
| 0.5% Sucrose Octasulfate | 0.60 |
| 1.0% Sucrose Octasulfate | 0.17 |
| 0.5% Chondroitin Sulfate A | 0.70 |
| 0.1% Chondroitin Sulfate A | 0.95 |
| 0.5% Chondroitin Sulfate B | 1.21 |
| 0.1% Chondroitin Sulfate C | 1.47 |
| 0.5% Chondroitin Sulfate C | 0.78 |
| 0.05% Myo-Inositol Hexasulfate | 0.85 |
| 0.5% Fucoidan | 0.88 |
| 0.5% Sulfated β-Cyclodextrin | 1.21 |
| 0.05% Sulfated β-Cyclodextrin | 1.00 |
| Osmolytes | |
| 27 mM L-Lysine hydrochloride | 1.31 |
| 30 mM sodium glutamate | 1.17 |
| 100 mM Glycine | 1.52 |
| 50 mM Glycine | 1.15 |
| Water-Soluble Polymers | |
| 0.5% Poly-L-Lysine | 2.78 |
| 0.5% Polyglutamic Acid | 2.57 |
| 0.05% Poly (lys, ala) | 1.90 |
| 0.5% Poly (lys, ala) | 0.80 |
| 0.05% Polyphosphoric Acid (sodium salt) | 0.79 |
| 0.05% Na-Tripolyphosphate (sodium salt) | 0.97 |
| Lyotropic Salts | |
| 0.05% Di-Na Di-H pyrophosphate | 0.93 |

TABLE III-continued

Amount of soluble IL-2 after two weeks of storage at 45° C. upon reconstitution.

| Reconstitution medium | Stability ratio |
| --- | --- |
| 0.2% Tetrasodium pyrophosphate | 0.82 |
| Surfactants | |
| 1.0% Pluronic | 0.65 |
| 0.5% Pluronic | 0.85 |
| 0.1% Tween-20 | 1.51 |
| 0.5% Tween-20 | 2.07 |
| 1.0% N-Octylglucoside | 0.50 |
| 0.01% N-Octylglucoside | 0.89 |
| 1.0% 2-Hydroxylpropyl-β-cyclodextrin | 1.46 |
| 0.5% 2-Hydroxylpropyl-β-cyclodextrin | 1.56 |
| Protein | |
| 0.5% Phosvitin | 0.85 |

As seen in Table III, samples containing the various reconstitution stabilizers show various levels of soluble rhKGF.

B. Buffers

Figure 4:
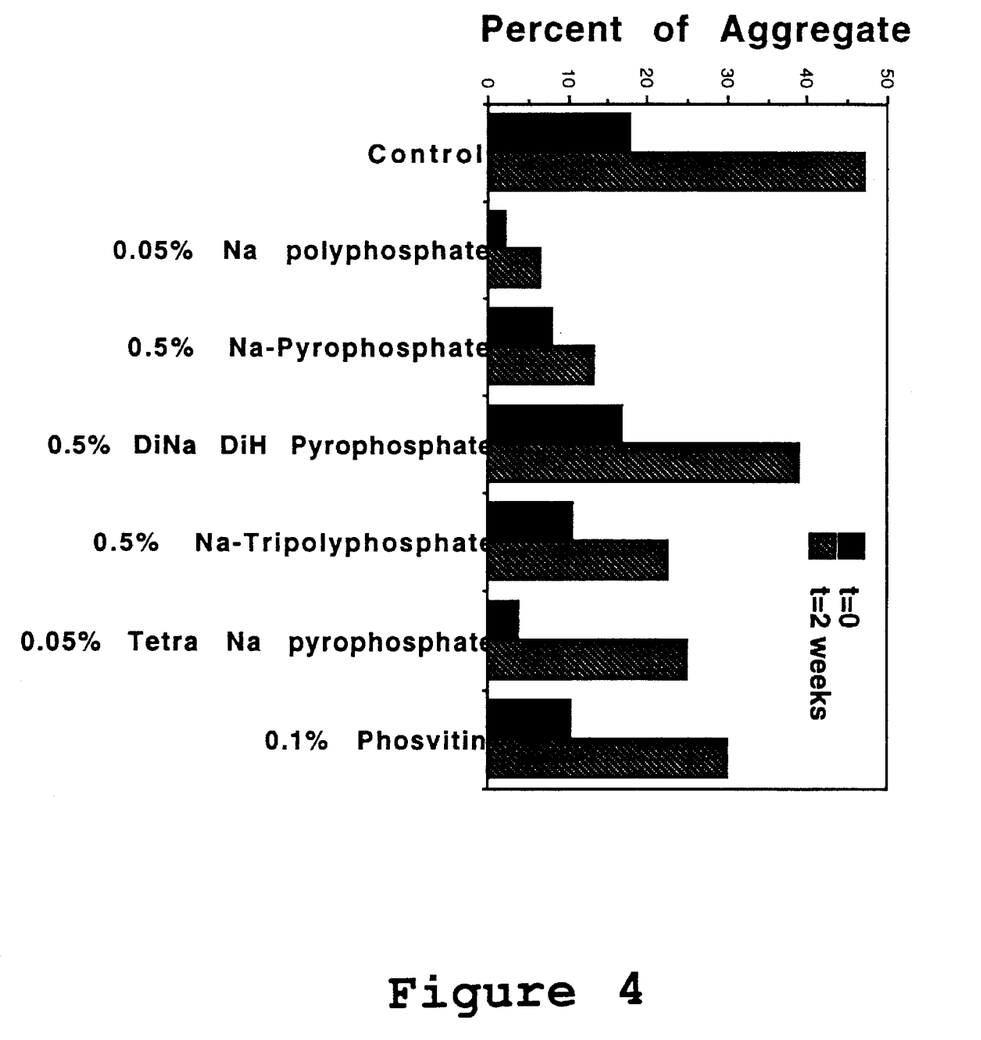
FIG. 4 shows the amount of aggregation for lyophilized KGF stored at 45° C. for two weeks upon reconstitution with 1 mL solution containing the pyrophosphates or polyphosphates. Lyophilized KGF samples contained 5% mannitol in 10 mM potassium phosphate buffer, pH 7.0. Each reconstituted sample was centrifuged (14000 g, 20 minutes at 4° C.) and the absorbance of the supernatant of the sample was obtained. The degree of aggregation (expressed as percent of aggregate) was calculated by comparing the percent of the absorbance of the supernatant to the absorbance of the pre-lyophilized sample.

IL-2 (0.8 mg/ml) was lyophilized from 1 mM MES buffer (pH 7.0). The lyophilized samples were then reconstituted with solutions buffered at two different pH's (4 and 7). Results are shown in FIG. 4. The samples rehydrated with diluents buffered at pH 4 showed significantly less aggregation than those rehydrated with diluents buffered at pH 7.0. Similar results were obtained with IL-2 lyophilized from 1 mM homopipes buffer (pH 4) followed by reconstitution with the same diluents (data not shown).

EXAMPLE 3

Effect of Reconstitution Stabilizers on RNase A Activity and Aggregation

Lyophilized RNase A in 100 mM sodium phosphate buffer, pH 10 was exposed to accelerated storage conditions (45° C. for 3 weeks) and the loss of soluble protein after reconstitution in the presence or absence of the additives was determined. The results are shown in Table IV.

TABLE IV

| Reconstitution Medium | Remaining Activity (%) (t = 45° C.) | Clarity |
| --- | --- | --- |
| Control | 61.9 | cloudy |
| 0.05% polyphosphoric acid | 96.5 | clear |
| 0.05% heparin (16K) | 60.2 | cloudy |
| 0.5% sulfated β-cyclodextrin | 77.0 | cloudy |

As seen in Table IV, RNase A showed a loss of enzymatic activity at various levels with the tested reconstitution stabilizers.

The foregoing invention has been described in some detail for purposes of clarity and understanding. It will also be obvious that various combinations in form and detail can be made without departing from the scope of the invention.

What is claimed is:

1. A process for preparing a formulation, which comprises admixing a dried protein with an effective amount of at least one reconstitution stabilizer under conditions effective to reduce aggregation of the dried protein upon reconstitution.

2. The process of claim 1, wherein the reconstitution stabilizer is selected from the group consisting of osmolytes, lyotropic salts, water-soluble synthetic and natural polymers, surfactants, sulfated polysaccharides, proteins and buffers.

3. The process of claim 2, wherein the reconstitution stabilizer is an osmolyte selected from the group consisting of amino acids, polyols, polyol acids, sugars, sugar alcohols and sugar acids.

4. The process of claim 3, wherein the osmolyte is an amino acid selected from the group consisting of histidine, salts of histidine, glycine, salts of aspartic acid, salts of glutamic acid, salts of lysine, salts of arginine, serine, proline and alanine.

5. The process of claim 3, wherein the osmolyte is a polyhydric alcohol selected from the group consisting of sorbitol, inositol, mannitol, xylitol and glycerol.

6. The process of claim 3, wherein the osmolyte is a sugar selected from the group consisting of trehalose, lactose, sucrose, glucose, galactose, maltose, mannose and fructose.

7. The process of claim 3, wherein the osmolyte is a methylamine selected from the group consisting of trimethylamine-N-oxide, N,N-dimethylglycine, amino-butyric acid, taurine, sarcosine, betaine or salts thereof.

8. The process of claim 2, wherein the reconstitution stabilizer is a lyotropic salt selected from the group consisting of imidazole, tetraalkylammonium, alkaline metal, alkaline earth metal or ammonium salts of organic acids or of mineral acids and pyrophosphates.

9. The process of claim 8, wherein the pyrophosphate is selected from the group consisting of disodium dihydropolyphosphate and tetrasodium polyphosphate.

10. The process of claim 2, wherein the reconstitution stabilizer is a water-soluble polymer.

11. The process of claim 10, wherein the water-soluble polymer is a synthetic polymer selected from the group consisting of polyethylene glycol, polyvinylpyrrolidene poly(acrylic acid) and polyphosphates.

12. The process of claim 11, wherein the polyphosphate is selected from the group consisting of sodium tripolyphosphate and sodium polyphosphate.

13. The process of claim 10, wherein the water-soluble polymer is a natural polymer selected from the group consisting of salts of polylysine, salts of polyaspartic acid, salts of polyglutamic acid, salts of polyarginine, salts of polyhistidine and polyornithine or salts thereof.

14. The process of claim 2, wherein the reconstitution stabilizer is a surfactant selected from the group consisting of pluronic, polyoxyethylene sorbitan mono-oleate, polyethylene mono-laureate, hydroxypropyl β-cyclodextrin and N-actylglucoside.

15. The process of claim 2, wherein the reconstitution stabilizer is a sulfated polysaccharide selected from the group consisting of heparin, heparan sulfate, dextran sulfate, sucrose octasulfate, sulfated β-cyclodextrin, myo-inositol hexasulfate, polypentosan sulfate, fucoidan, chondroitin sulfate A, chondroitin sulfate B, chondroitin sulfate C and derivatives thereof.

16. The process of claim 2, wherein the reconstitution stabilizer is a carrier protein selected from the group consisting of phosvitin and albumin.

17. The process of claim 2, wherein the reconstitution stabilizer is a buffer selected from the group consisting of homopipes, morpholinoethane sulfonic acid, acetate, citrate and glycine.

18. The process according to claim 1, wherein the formulation is an aqueous medicinal formulation single dose administration unit comprising an effective amount of a dried therapeutic protein and from 1 to 5 ml of a physiologically acceptable solvent.

19. The process of claim 18, wherein the concentration of dried protein in the aqueous medicinal formulation is within the range of from about 0.01 to about 20,000 micrograms per milliliter (μγ/ml).

20. The process of claim 18, wherein the dried protein and solvent are mixed for a period of between about 1 to 30 minutes.

21. The process of claim 18, wherein the dried protein and solvent are mixed at a temperature of between about 2° C. to 50° C.

22. The process of claim 1, wherein the dried protein is dried by lyophilization.

23. The process of claim 1, wherein the dried protein is keratinocyte growth factor.

24. A kit for preparing an aqueous protein formulation comprising a first container having a dried protein and a second container having a reconstitution stabilizer.

25. The kit of claim 24, wherein the first container has an effective amount of a dried therapeutic protein and the second container has the reconstitution stabilizer dissolved in a physiologically acceptable solvent, whereby a single dose administration unit of an aqueous medicinal formulation is prepared upon combining the contents of the first and second containers.

* * * * *

UNITED STATES PATENT AND TRADEMARK OFFICE
CERTIFICATE OF CORRECTION

PATENT NO. : 5,580,856  Page 1 of 1
DATED : December 3, 1996
INVENTOR(S) : Prestrelski et al.

It is certified that error appears in the above-identified patent and that said Letters Patent is hereby corrected as shown below:

<u>Column 14,</u>
Line 36, change "polyvinylpyrrolidene" to -- polyvinylpyrroidone --.

Signed and Sealed this

Twenty-second Day of April, 2003

JAMES E. ROGAN
*Director of the United States Patent and Trademark Office*